(12) United States Patent
Moua

(10) Patent No.: US 11,090,111 B2
(45) Date of Patent: *Aug. 17, 2021

(54) SURGICAL INSTRUMENT WITH SWITCH ACTIVATION CONTROL

(71) Applicant: COVIDIEN LP, Mansfield, MA (US)

(72) Inventor: Tony Moua, Broomfield, CO (US)

(73) Assignee: COVIDIEN LP, Mansfield, MA (US)

(*) Notice: Subject to any disclaimer, the term of this patent is extended or adjusted under 35 U.S.C. 154(b) by 141 days.

This patent is subject to a terminal disclaimer.

(21) Appl. No.: 16/417,950

(22) Filed: May 21, 2019

(65) Prior Publication Data

US 2019/0269454 A1 Sep. 5, 2019

Related U.S. Application Data

(63) Continuation of application No. 15/226,650, filed on Aug. 2, 2016, now Pat. No. 10,335,228, which is a
(Continued)

(51) Int. Cl.
*A61B 18/14* (2006.01)
*A61B 17/28* (2006.01)
(Continued)

(52) U.S. Cl.
CPC ........ *A61B 18/1445* (2013.01); *A61B 17/282* (2013.01); *A61B 18/1206* (2013.01);
(Continued)

(58) Field of Classification Search
CPC .............. A61B 17/282; A61B 18/1206; A61B 18/1445; A61B 2018/1445;
(Continued)

(56) References Cited

U.S. PATENT DOCUMENTS 3,100,489 A 8/1963 Bagley
D249,549 S 9/1978 Pike
(Continued)

FOREIGN PATENT DOCUMENTS

CN 201299462 Y 9/2009
CN 203736305 U 7/2014
(Continued)

OTHER PUBLICATIONS

European Search Report from Application No. EP14158818.6 dated May 28, 2014.
(Continued)

*Primary Examiner* — Michael F Peffley
(74) *Attorney, Agent, or Firm* — Carter, DeLuca & Farrell LLP

(57) ABSTRACT

A surgical instrument includes a housing and an elongated shaft operably coupled to an actuating mechanism moveable between an actuated position and an unactuated position. An end effector includes a pair of opposing first and second jaw members and is adapted to connect to a source of electrosurgical energy. A switch is moveable between an activated position to initiate delivery of electrosurgical energy to the end effector and a deactivated position to terminate delivery of electrosurgical energy to the end effector. A switch activation member is configured to move the switch between an activated position and a deactivated position. A switch control member is configured to maintain the switch in the activated position during at least partial movement of the actuating mechanism from the actuated position to the unactuated position.

20 Claims, 13 Drawing Sheets

Related U.S. Application Data continuation of application No. 14/105,374, filed on Dec. 13, 2013, now Pat. No. 9,456,863.

(60) Provisional application No. 61/776,185, filed on Mar. 11, 2013.

(51) Int. Cl.
  *A61B 18/12* (2006.01)
  *A61B 18/00* (2006.01)

(52) U.S. Cl.
  CPC .............. *A61B 2018/00607* (2013.01); *A61B 2018/00916* (2013.01); *A61B 2018/1455* (2013.01)

(58) Field of Classification Search
  CPC ........... A61B 2018/00607; A61B 2018/00916; A61B 2018/1455
  See application file for complete search history.

(56) References Cited

U.S. PATENT DOCUMENTS

| | | |
|---|---|---|
| D263,020 S | 2/1982 | Rau, III |
| 4,461,297 A | 7/1984 | Sutter |
| 4,461,305 A | 7/1984 | Cibley |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,122,139 A | 6/1992 | Sutter |
| 5,211,655 A | 5/1993 | Hasson |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,383,875 A | 1/1995 | Bays et al. |
| D358,887 S | 5/1995 | Feinberg |
| 5,454,827 A | 10/1995 | Aust et al. |
| 5,478,351 A | 12/1995 | Meade et al. |
| 5,512,721 A | 4/1996 | Young et al. |
| 5,601,601 A | 2/1997 | Tal et al. |
| D384,413 S | 9/1997 | Zlock et al. |
| 5,746,739 A | 5/1998 | Sutter |
| H1745 H | 8/1998 | Paraschac |
| D402,028 S | 12/1998 | Grimm et al. |
| D408,018 S | 4/1999 | McNaughton |
| 5,891,140 A | 4/1999 | Ginn et al. |
| 5,891,142 A | 4/1999 | Eggers et al. |
| D416,089 S | 11/1999 | Barton et al. |
| 6,010,516 A | 1/2000 | Hulka |
| D424,694 S | 5/2000 | Tetzlaff et al. |
| D425,201 S | 5/2000 | Tetzlaff et al. |
| 6,106,542 A | 8/2000 | Toybin et al. |
| 6,117,158 A | 9/2000 | Measamer et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,613 B2 | 8/2006 | Treat |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,166,106 B2 | 1/2007 | Bartel et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| 7,211,079 B2 | 5/2007 | Treat |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,628,791 B2 * | 12/2009 | Garrison ............ A61B 18/1445 606/51 |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,922,718 B2 | 4/2011 | Moses et al. |
| D649,249 S | 11/2011 | Guerra |
| D649,643 S | 11/2011 | Allen, IV et al. |
| 8,152,806 B2 | 4/2012 | Black et al. |
| D661,394 S | 6/2012 | Romero et al. |
| 8,679,140 B2 | 3/2014 | Butcher |
| RE44,834 E | 4/2014 | Dumbauld et al. |
| 8,939,973 B2 | 1/2015 | Garrison et al. |
| 8,945,126 B2 | 2/2015 | Garrison et al. |
| 8,945,127 B2 | 2/2015 | Garrison et al. |
| 9,113,907 B2 | 8/2015 | Allen, IV et al. |
| 9,113,937 B2 | 8/2015 | Collings et al. |
| 9,119,630 B2 | 9/2015 | Townsend et al. |
| 9,124,013 B2 | 9/2015 | Frushhour et al. |
| 9,161,769 B2 | 10/2015 | Stoddard et al. |
| 9,192,421 B2 | 11/2015 | Garrison |
| 9,241,732 B2 | 1/2016 | Craig |
| 9,259,266 B2 | 2/2016 | Schmaltz et al. |
| 9,265,566 B2 | 2/2016 | O'Neill et al. |
| 9,368,004 B2 | 6/2016 | Plaven |
| 9,375,205 B2 | 6/2016 | Mueller |
| 9,375,227 B2 | 6/2016 | Garrison et al. |
| 9,375,256 B2 | 6/2016 | Cunningham et al. |
| 9,375,259 B2 | 6/2016 | Payne et al. |
| 9,375,260 B2 | 6/2016 | Kerr |
| 9,375,262 B2 | 6/2016 | Reschke et al. |
| 9,433,461 B2 | 9/2016 | Arya et al. |
| 9,456,863 B2 | 10/2016 | Moua |
| 9,480,522 B2 | 11/2016 | Horner et al. |
| 9,498,281 B2 | 11/2016 | Kendrick |
| 9,526,564 B2 | 12/2016 | Rusin |
| 9,549,749 B2 | 1/2017 | Kendrick |
| 9,572,529 B2 | 2/2017 | Latimer et al. |
| 9,636,168 B2 | 5/2017 | Payne et al. |
| 9,681,908 B2 | 6/2017 | Garrison |
| 9,713,491 B2 | 7/2017 | Roy et al. |
| 9,839,467 B2 | 12/2017 | Harper et al. |
| 9,877,775 B2 | 1/2018 | Hart |
| 10,070,916 B2 * | 9/2018 | Artale ................ A61B 18/1445 |
| 10,206,583 B2 | 2/2019 | Nau, Jr. |
| 10,226,297 B2 | 3/2019 | Nau, Jr. |
| 10,231,782 B2 | 3/2019 | Nau, Jr. |
| 10,335,228 B2 | 7/2019 | Moua |
| 2003/0018331 A1 | 1/2003 | Dycus et al. |
| 2003/0109875 A1 | 6/2003 | Tetzlaff et al. |
| 2003/0171747 A1 | 9/2003 | Kanehira et al. |
| 2003/0229344 A1 | 12/2003 | Dycus et al. |
| 2004/0176762 A1 | 9/2004 | Lawes et al. |
| 2004/0243125 A1 | 12/2004 | Dycus et al. |
| 2005/0154387 A1 | 7/2005 | Moses et al. |
| 2006/0064085 A1 | 3/2006 | Schechter et al. |
| 2007/0043352 A1 | 2/2007 | Garrison et al. |
| 2007/0260241 A1 | 11/2007 | Dalla Betta et al. |
| 2008/0114349 A1 | 5/2008 | Treat |

(56) References Cited

U.S. PATENT DOCUMENTS

| | | |
|---|---|---|
| 2008/0125768 A1 | 5/2008 | Tahara et al. |
| 2008/0215048 A1 | 9/2008 | Hafner et al. |
| 2008/0262491 A1 | 10/2008 | Swoyer et al. |
| 2009/0018536 A1 | 1/2009 | Behnke |
| 2010/0030205 A1 | 2/2010 | Herzon |
| 2011/0184459 A1 | 7/2011 | Malkowski et al. |
| 2011/0190765 A1 | 8/2011 | Chojin |
| 2011/0251613 A1 | 10/2011 | Guerra et al. |
| 2011/0301592 A1 | 12/2011 | Kerr et al. |
| 2012/0022524 A1 | 1/2012 | Timm et al. |
| 2012/0022529 A1 | 1/2012 | Shelton, IV et al. |
| 2012/0136347 A1 | 5/2012 | Brustad et al. |
| 2012/0136354 A1 | 5/2012 | Rupp |
| 2013/0018411 A1 | 1/2013 | Collings et al. |
| 2014/0094798 A1 | 4/2014 | Garrison et al. |
| 2014/0100564 A1 | 4/2014 | Garrison |
| 2014/0100569 A1 | 4/2014 | Lawes et al. |
| 2014/0107443 A1 | 4/2014 | Hoarau et al. |
| 2014/0135763 A1 | 5/2014 | Kappus et al. |
| 2014/0194875 A1 | 7/2014 | Reschke et al. |
| 2014/0221994 A1 | 8/2014 | Reschke |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| EP | 1645238 A1 | 4/2006 |
| EP | 1810625 A1 | 7/2007 |
| EP | 2316365 A2 | 5/2011 |
| EP | 2347725 A1 | 7/2011 |
| EP | 2436330 A1 | 4/2012 |
| EP | 2659848 A2 | 11/2013 |
| EP | 2659849 A3 | 1/2014 |
| JP | 61501068 A | 5/1986 |
| JP | 1024051 | 1/1989 |
| JP | 1147150 | 6/1989 |
| JP | 55106 | 1/1993 |
| JP | 0540112 A | 2/1993 |
| JP | 6121797 | 5/1994 |
| JP | 6285078 A | 10/1994 |
| JP | 06343644 | 12/1994 |
| JP | 6511401 A | 12/1994 |
| JP | 07265328 | 10/1995 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |
| JP | 9122138 A | 5/1997 |
| JP | 0010000195 A | 1/1998 |
| JP | 10155798 A | 6/1998 |
| JP | 11047149 | 2/1999 |
| JP | 11070124 A | 3/1999 |
| JP | 11169381 A | 6/1999 |
| JP | 11192238 A | 7/1999 |
| JP | 11244298 | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 2012106009 A | 6/2012 |
| JP | 0006030945 B2 | 11/2016 |
| JP | 6502328 B2 | 4/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |
| WO | 2011044343 A2 | 4/2011 |

OTHER PUBLICATIONS

The extended European Search Report from Application No. 14158819.4 dated Jun. 10, 2014.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).

(56) References Cited

OTHER PUBLICATIONS

Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for be Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA , Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C..
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Schmaltz et al.
Chinese Office Action from Appl. No. CN 201410048138.9 dated Feb. 4, 2017.
European Examination Report from Appl. No. EP 15184940.3 dated Jan. 27, 2017.
U.S. Appl. No. 09/591,328, filed Jun. 9, 2000, Ryan et al.
U.S. Appl. No. 12/336,970, filed Dec. 17, 2008, Sremcich et al.
U.S. Appl. No. 13/731,674, filed Dec. 31, 2012, Siebrecht.
Extended European Search Report from European Appl. No. 15184940.3 dated Dec. 22, 2015 (7 pages).
Austrlalian Examination Report issued in Appl. No. AU 2014200225 dated Aug. 2, 2017.

* cited by examiner

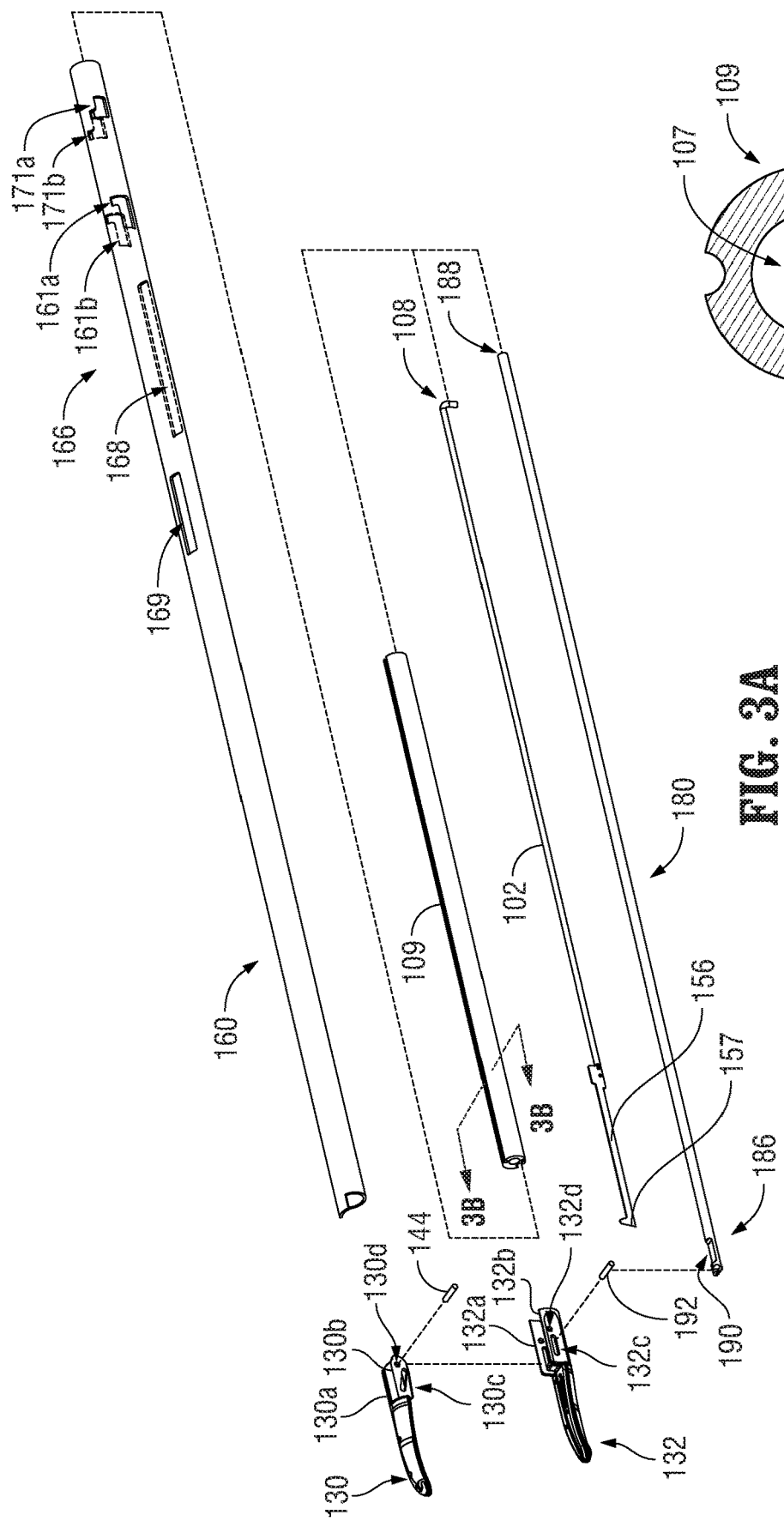
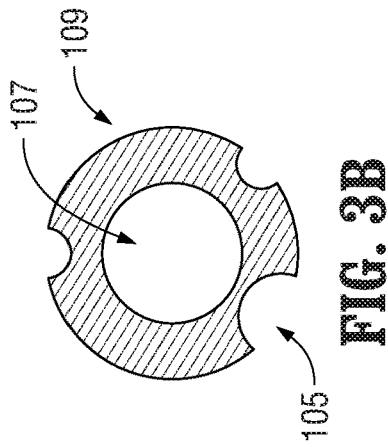
FIG. 3A
FIG. 3B

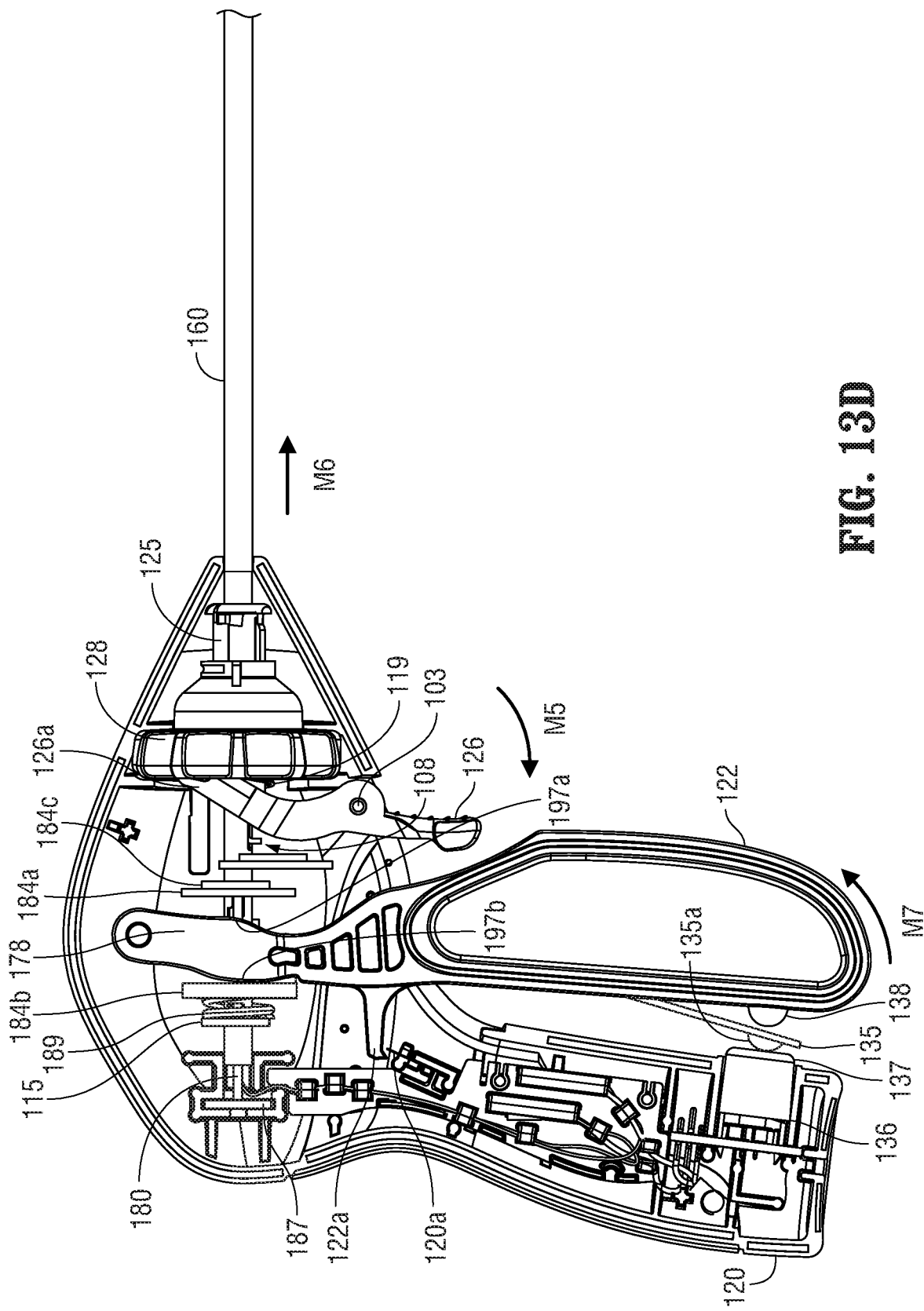

US 11,090,111 B2

SURGICAL INSTRUMENT WITH SWITCH ACTIVATION CONTROL

CROSS-REFERENCE TO RELATED APPLICATIONS

This application is a continuation of U.S. patent application Ser. No. 15/226,650, filed on Aug. 2, 2016, now U.S. Pat. No. 10,335,228, which is a continuation of U.S. patent application Ser. No. 14/105,374, filed on Dec. 13, 2013, now U.S. Pat. No. 9,456,863, which claims the benefit of the filing date of provisional U.S. Patent Application No. 61/776,185, filed on Mar. 11, 2013, the entire contents of each of which are incorporated herein by reference.

INTRODUCTION

The present disclosure relates generally to the field of surgical instruments. In particular, the present disclosure relates to an endoscopic electrosurgical forceps that includes a system and method for controlling the activation and deactivation of treatment energy.

BACKGROUND

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaws. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 kg/cm$^2$ to about 16 kg/cm$^2$.

SUMMARY

The present disclosure relates generally to the field of surgical instruments. In particular, the present disclosure relates to an endoscopic electrosurgical forceps that includes a system and method for controlling the activation and deactivation of treatment energy.

As is traditional, the term "distal" refers herein to an end of the apparatus that is farther from an operator, and the term "proximal" refers herein to the end of the electrosurgical forceps that is closer to the operator.

According to one aspect of the present disclosure, a surgical instrument is provided. The surgical instrument includes a housing and an elongated shaft. The elongated shaft has a distal portion extending from the housing and a proximal portion coupled to the housing. A longitudinal axis is defined through the elongated shaft. An actuating mechanism is operably coupled to the elongated shaft and is moveable relative to the housing between an actuated position and an unactuated position to selectively move the elongated shaft along the longitudinal axis. An end effector includes a pair of opposing first and second jaw members movable relative to each other from a first position wherein the jaw members are disposed in spaced relation relative to one another to a second position wherein the jaw members cooperate to grasp tissue. The end effector is adapted to connect to a source of electrosurgical energy for conducting electrosurgical energy through tissue grasped between the jaw members to effect a tissue seal. A switch is supported by the housing and moveable between an activated position to initiate delivery of electrosurgical energy from the electrosurgical energy source to the end effector and a deactivated position to terminate delivery of electrosurgical energy from the electrosurgical energy source to the end effector. A switch activation member is disposed on the actuating mechanism and is configured to move the switch to the activated position upon movement of the actuating mechanism to the actuated position and to the deactivated position upon movement of the actuating mechanism to the unactuated position. A switch control member is configured to maintain the switch in the activated position during at least partial movement of the actuating mechanism from the actuated position to the unactuated position.

Additionally or alternatively, the surgical instrument may also include a knife blade supported in the elongated shaft and moveable in a longitudinal direction through a knife channel defined along a length of at least one of the jaw members to cut tissue disposed between the jaw members.

Additionally or alternatively, the switch may be operably coupled to a depressible button extending from the housing and configured to be selectively engaged by the switch activation member upon movement of the actuating mechanism to the actuated position.

Additionally or alternatively, the switch control member may include a biasing member disposed between the depressible button and the switch. The biasing member may be configured to maintain a force on the switch to maintain the switch in the activated position during at least partial movement of the actuating mechanism from the actuated position to the unactuated position.

Additionally or alternatively, the switch control member may include a biasing member extending from the actuating mechanism and having a button activation post configured to engage the depressible button. The biasing member may be configured to maintain a force on the switch to maintain the switch in the activated position during at least partial movement of the actuating mechanism from the actuated position to the unactuated position.

Additionally or alternatively, the switch control member may include a biasing member disposed between the depressible button and the switch. The depressible button may have a switch activation post extending therefrom at least partially through the biasing member. The biasing member may be configured to maintain a force on the switch to maintain the switch in the activated position during at least partial movement of the actuating mechanism from the actuated position to the unactuated position.

Additionally or alternatively, the switch control member may include a biasing member extending from the actuating mechanism configured to maintain a force on the switch to maintain the switch in the activated position during at least partial movement of the actuating mechanism from the actuated position to the unactuated position.

Additionally or alternatively, the second jaw member may be mechanically coupled to a distal end of the elongated shaft and the first jaw member may be configured to move relative to the second jaw member.

Additionally or alternatively, the switch control member may include a leaf spring.

Additionally or alternatively, the switch control member may include a coiled spring.

Additionally or alternatively, the surgical instrument may also include a stationary actuation member axially disposed within the elongated shaft. The stationary actuation member may include a cam pin mechanically coupled to the distal portion of the elongated shaft. One or both of the first and second jaw members may include a camming slot configured to engage the cam pin to move the at least one movable jaw member about a pivot between the first position and the second position upon movement of the elongated shaft along the longitudinal axis.

Additionally or alternatively, an electrical insulator may be coupled to one or both of the jaw members.

Additionally or alternatively, the surgical instrument may also include an electrically conductive tissue sealing surface extending along a length of at least one jaw member and adapted to connect to the source of electrosurgical energy.

According to another aspect of the present disclosure, a surgical instrument is provided. The surgical instrument includes a housing and an elongated shaft. The elongated shaft has a distal portion extending from the housing and a proximal portion coupled to the housing. A longitudinal axis is defined through the elongated shaft. An actuating mechanism is operably coupled to the elongated shaft and is moveable relative to the housing between an actuated position and an unactuated position to selectively move the elongated shaft along the longitudinal axis. An end effector includes a pair of opposing first and second jaw members movable relative to each other from a first position wherein the jaw members are disposed in spaced relation relative to one another to a second position wherein the jaw members cooperate to grasp tissue. The end effector is adapted to connect to a source of electrosurgical energy for conducting electrosurgical energy through tissue grasped between the jaw members to effect a tissue seal. A switch is supported by the housing and moveable between an activated position to initiate delivery of electrosurgical energy from the electrosurgical energy source to the end effector and a deactivated position to terminate delivery of electrosurgical energy from the electrosurgical energy source to the end effector. A switch activation member is disposed on the actuating mechanism and is configured to move the switch to the activated position upon movement of the actuating mechanism to the actuated position and to the deactivated position upon movement of the actuating mechanism to the unactuated position. A switch control member is configured to maintain the switch in the activated position during at least partial movement of the actuating mechanism from the actuated position to the unactuated position. A knife blade is supported in the elongated shaft and is moveable in a longitudinal direction through a knife channel defined along a length of at least one of the jaw members to cut tissue disposed between the jaw members.

Additionally or alternatively, the switch may be operably coupled to a depressible button extending from the housing and configured to be selectively engaged by the switch activation member upon movement of the actuating mechanism to the actuated position.

Additionally or alternatively, the switch control member may be disposed between the depressible button and the switch.

Additionally or alternatively, the switch control member may be disposed on the actuating mechanism.

According to another aspect of the present disclosure, a switch actuation control mechanism for an electrosurgical instrument having a housing and an end effector adapted to connect to a source of electrosurgical energy for conducting electrosurgical energy through tissue grasped by the end effector to effect a tissue seal is provided. The switch actuation control mechanism including a switch supported by the housing. The switch is moveable between an activated position to initiate delivery of electrosurgical energy from the electrosurgical generator to the end effector and a deactivated position to terminate delivery of electrosurgical energy from the electrosurgical generator to the end effector. A switch activation member is moveable between an actuated position and an unactuated position to selectively move the switch between the activated position and the deactivated position. A switch control member is configured to maintain the switch in the activated position during at least partial movement of the switch activation member from the actuated position to the unactuated position.

Additionally or alternatively, the switch control member may be disposed between the switch and the switch activation member.

Additionally or alternatively, the switch control member may include a biasing member configured to maintain a force on the switch to maintain the switch in the activated position during at least partial movement of the switch activation member from the actuated position to the unactuated position.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 3A is a perspective view of the end effector and elongated shaft of FIG. 1 with parts separated;

FIG. 3B is cross-sectional view taken along line 3B-3B of FIG. 3A showing a distal portion of the electrosurgical forceps of FIG. 1 depicting a tube guide;

FIG. 13D is an internal, side view of the proximal portion of the instrument of FIG. 10 depicting the knife trigger in an actuated configuration, which corresponds to an actuated or distal position of the knife with respect to the jaw members.

DETAILED DESCRIPTION

Figure 1:
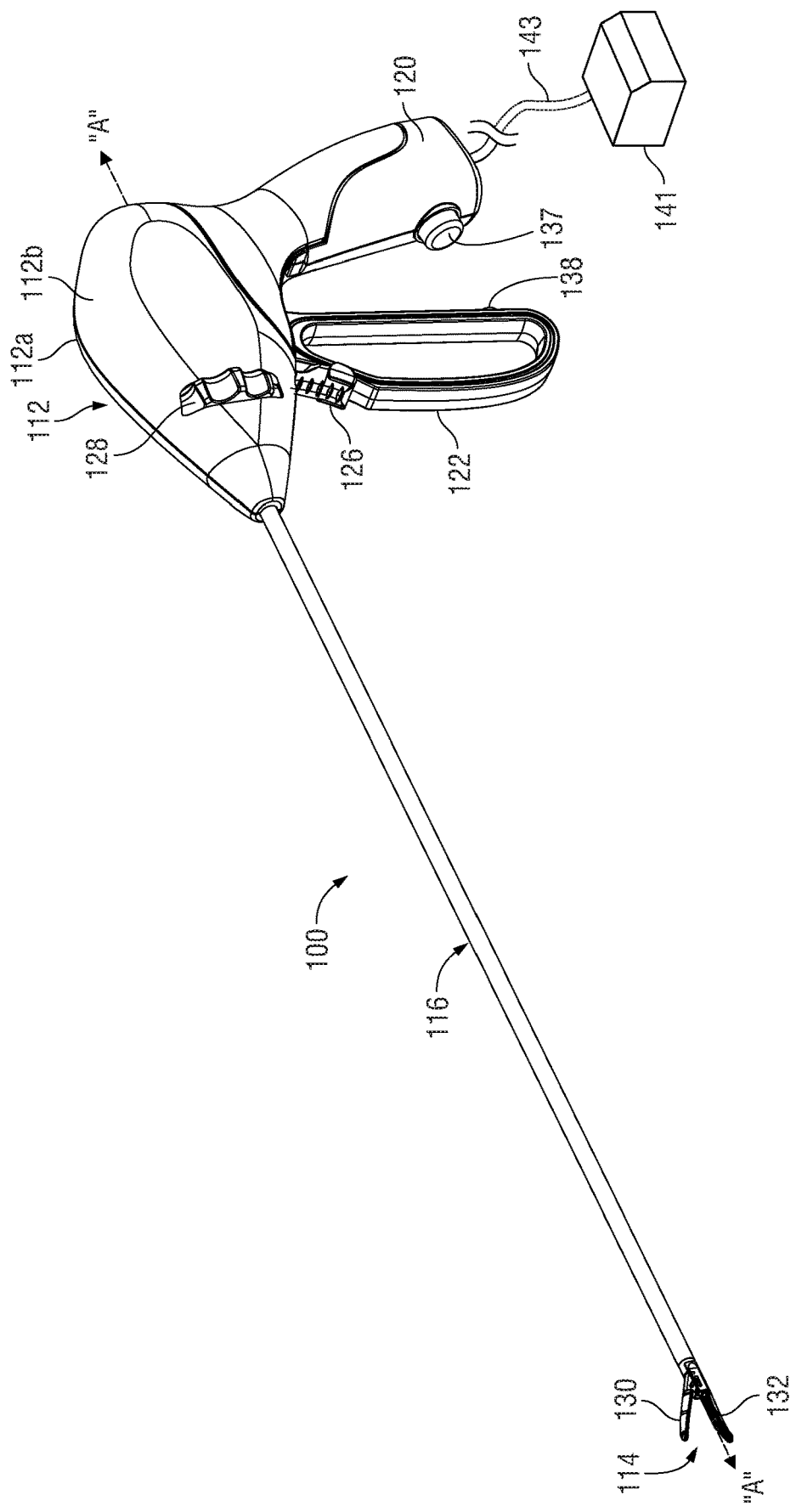
FIG. 1 is a perspective view of an electrosurgical forceps according to an embodiment of the present disclosure including a housing, an elongated shaft, and an end effector.

Referring initially to FIG. 1, an embodiment of an electrosurgical forceps 100 generally includes a housing 112 that supports various actuators thereon for remotely controlling an end effector 114 through an elongated shaft 116. Although this configuration is typically associated with instruments for use in laparoscopic or endoscopic surgical procedures, various aspects of the present disclosure may be practiced with traditional open instruments and in connection with certain endoluminal procedures.

The housing 112 is constructed of a left housing half 112a and a right housing half 112b. The left and right designation of the housing halves 112a, 112b refer to the respective directions as perceived by an operator using the forceps 100. The housing halves 112a, 112b are constructed of sturdy plastic, and are joined to one another by adhesives, ultrasonic welding or other suitable assembly methods.

To mechanically control the end effector 114, the housing 112 supports a stationary handle 120, a movable handle 122, a trigger 126 and a rotation knob 128. The movable handle 122 is operable to move the end effector 114 between an open configuration (FIG. 2A) wherein a pair of opposed jaw members 130, 132 are disposed in spaced relation relative to one another, and a closed or clamping configuration (FIG. 2B) wherein the jaw members 130, 132 are closer together. Approximation of the movable handle 122 with the stationary handle 120 serves to move the end effector 114 to the closed configuration and separation of the movable handle 122 from the stationary handle 120 serves to move the end effector 114 to the open configuration. The trigger 126 is operable to extend and retract a knife blade 156 (see FIGS. 2A and 2B) through the end effector 114 when the end effector 114 is in the closed configuration. The rotation knob 128 serves to rotate the elongated shaft 116 and the end effector 114 about a longitudinal axis A-A extending through the forceps.

To electrically control the end effector 114, the stationary handle 120 supports a depressible button 137 thereon, which is operable by the user to initiate and terminate the delivery of electrosurgical energy to the end effector 114. More specifically, and as illustrated in FIGS. 13A-13D, the depressible button 137 is mechanically coupled to a switch 136 disposed within the stationary handle 120. In some embodiments, the button 137 is engageable by a button activation post 138 extending from a proximal side of the moveable handle 122 upon proximal movement of the moveable handle 122. The switch 136 is in electrical communication with a source of electrosurgical energy such as electrosurgical generator 141 or a battery (not shown) supported within the housing 112. The generator 141 may include devices such as the LIGASURE® Vessel Sealing Generator and the Force Triad® Generator sold by Covidien Energy-based Devices of Boulder, Colo. A cable 143 extends between the housing 112 and the generator 141 and includes a connector (not shown) thereon such that the forceps 100 may be selectively coupled and decoupled electrically from the generator 141.

As further detailed hereinbelow, a user squeezes moveable handle 122 to approximate the moveable handle 122 with the stationary handle 120 and activate the switch 136 to initiate the delivery of electrosurgical energy to the end effector 114 and effect a tissue seal. Upon completion of a tissue seal, the user operates the trigger 126 to advance the knife blade 156 through the end effector 114 when the end effector 114 is in the closed configuration. As the user reaches for the trigger 126 with the same hand that is squeezing the moveable handle 122 to keep the end effector 114 in the closed configuration, the moveable handle 122 may inadvertently move distally away from the stationary handle 120. This distal movement of the moveable handle 122 may cause the button activation post 138 to disengage the button 137 and, in turn, the button 137 disengages and deactivates the switch 136 to terminate delivery of electrosurgical energy to the end effector 114. When the user moves the trigger 126 proximally to advance the knife blade 156 through the end effector 114, the user re-squeezes the moveable handle 122 such that button activation post 138 reengages and depresses the button 137, thereby reactivating the switch 136. Reactivation of the switch 136 reinitiates the delivery of electrosurgical energy to the end effector 114 while the knife blade 156 is advanced through the end effector 114.

Figure 10:
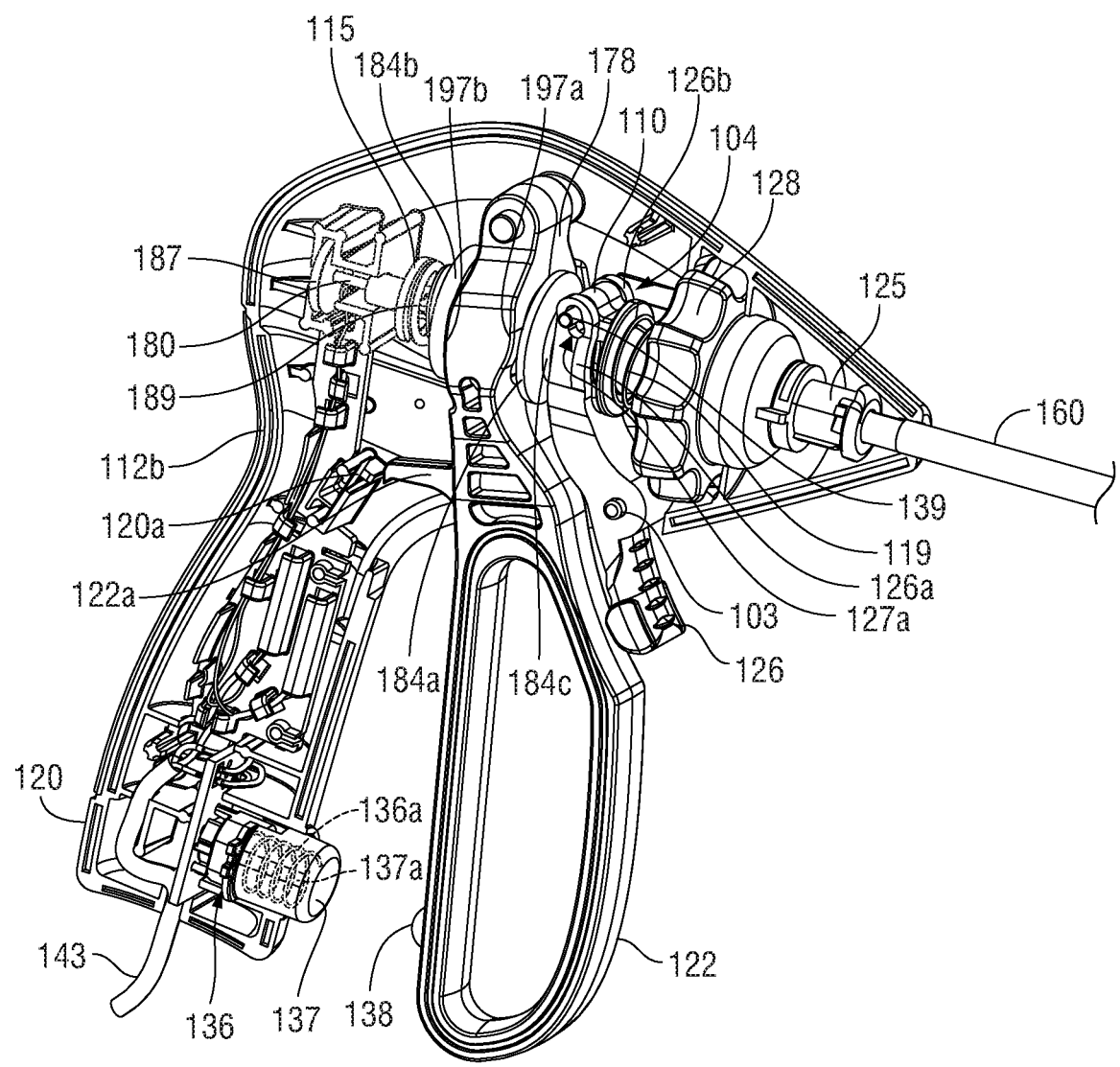
FIG. 10 is a perspective view of a proximal portion of the instrument of FIG. 1 with a portion of the housing removed revealing internal components.

In some embodiments, the forceps 100 may include an enhanced switch control feature configured to prevent the deactivation and reactivation of the switch 136 to terminate and reinitiate, respectively, the delivery of electrosurgical energy to the end effector 114 during operation of the trigger 126. With reference to FIG. 10, one such embodiment is depicted, wherein the button 137 includes a switch activation post 137a extending therefrom and a biasing member 136a (e.g., a coiled spring) disposed about the switch activation post 137a between the switch 136 and the button 137. Switch activation post 137a is positioned relative to the switch 136 such that when button activation post 138 engages and depresses button 137 upon approximation of moveable handle 122 with stationary handle 120, switch activation post 137a engages and activates switch 136. Depression of button 137 also causes biasing member 136a to compress between the button 137 and the switch 136 and to apply a spring force on switch 136. If the moveable handle 122 inadvertently moves distally away from the stationary handle 120 during operation of the trigger 126, the biasing member 136a, although now slightly decompressed, serves to mitigate the effects of this distal movement of the moveable handle 122 by maintaining a spring force on the switch 136. This spring force maintained on the switch 136 is sufficient to keep the switch 136 activated during at least a portion of travel of the moveable handle 122 in the distal direction, such that the switch 136 is not deactivated and reactivated during operation of the trigger 126. As the moveable handle 122 moves farther away from the stationary handle 120 to move the end effector 114 to the open configuration (FIG. 2A), the spring force maintained on the switch 136 by the biasing member 136a relents and, as a result, the switch 136 is deactivated.

Figure 2A:
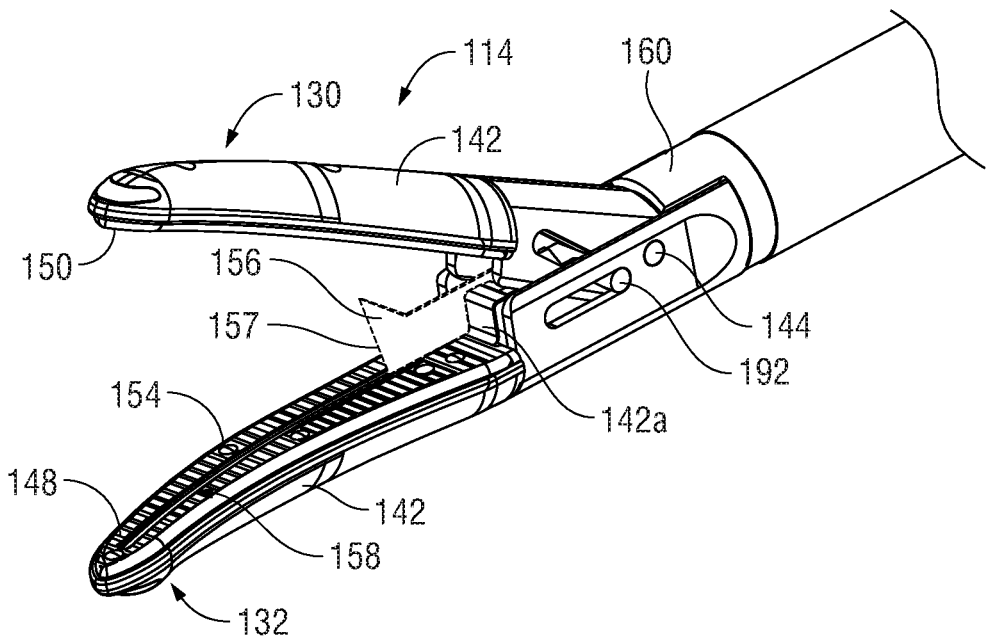
FIG. 2A is an enlarged, perspective view of the end effector of FIG. 1 depicted with a pair of jaw members in an open configuration.
Figure 2B:
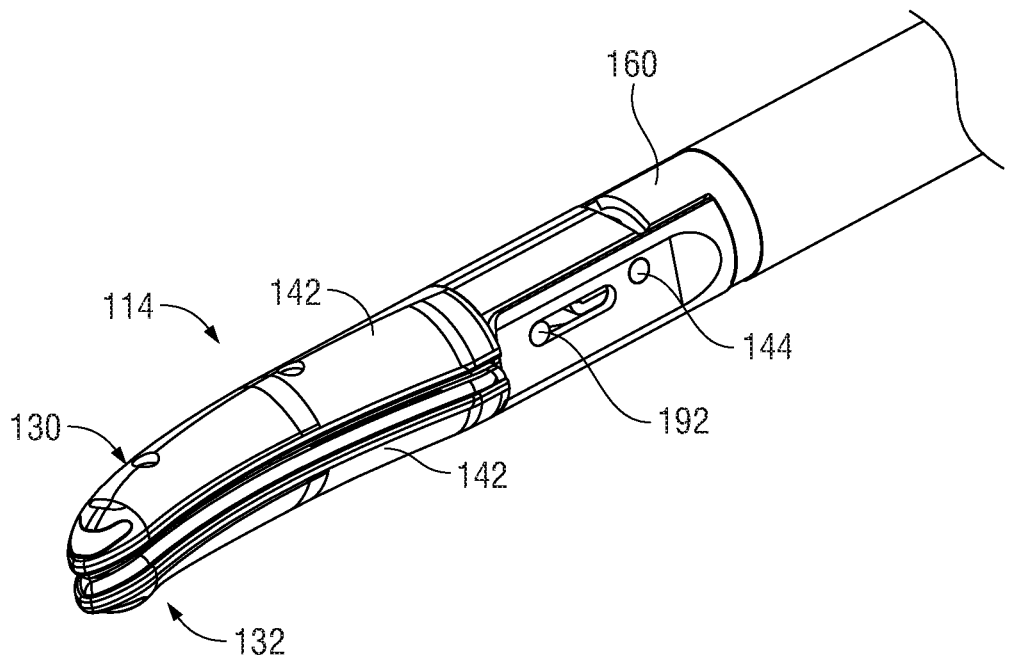
FIG. 2B is an enlarged, perspective view of the end effector of FIG. 1 depicted with the pair of jaw members in a closed configuration.

Referring now to FIGS. 2A-3, the end effector 114 may be moved from the open configuration (FIG. 2A) wherein tissue (not shown) is received between the jaw members 130, 132, and the closed configuration (FIG. 2B), wherein the tissue is clamped and treated. The upper and lower jaw members 130, 132 are electrically coupled to cable 143, and thus to the generator 141 (e.g., via a respective wire extending through the elongated shaft 116) to provide an electrical pathway to a pair of electrically conductive, tissue-engaging sealing plates 148, 150 disposed on the lower and upper jaw members 132, 130, respectively. The sealing plate 148 of the lower jaw member 132 opposes the sealing plate 150 of the upper jaw member 130, and, in some embodiments, the sealing plates 148 and 150 are electrically coupled to opposite terminals, e.g., positive or active (+) and negative or return (−) terminals associated with the generator 141. Thus, bipolar energy may be provided through the sealing plates 148 and 150. Alternatively, the sealing plates 148 and 150 and/or the end effector 114 may be configured for delivering monopolar energy to the tissue. In a monopolar configuration, one or both sealing plates 148 and 150 deliver electrosurgical energy from an active terminal, e.g. (+), while a return pad (not shown) is placed generally on a patient and provides a return path to the opposite terminal, e.g. (−), of the generator 141. Each jaw member 130, 132 includes a jaw insert 140 and an insulator 142 that serves to electrically insulate the sealing plates 150, 148 from the jaw insert 140 of jaw members 130, 132, respectively.

Referring to FIG. 3, the elongated shaft 116 includes various longitudinal components that operatively couple the end effector 114 to the various actuators supported by the housing 112 (FIG. 1). An outer shaft member 160 defines an exterior surface of the elongated shaft 116 and supports movement of other components therethrough as described below. The outer shaft member 160 is configured for longitudinal motion with respect to an inner actuation member 180 axially received within the outer shaft member 160. The inner actuation member 180 may be a rod, shaft, stamped metal, or other suitable mechanical component. A proximal portion 166 of the outer shaft member 160 is configured for receipt within the housing 112 (FIG. 1), and includes features for operatively coupling the outer shaft member 160 to the actuators supported thereon, e.g. the movable handle 122. A distal portion 186 of the inner actuation member 180 includes a longitudinal recess 190 defined therein that provides clearance for the pivot pin 144 and thus, permits longitudinal reciprocation of the pivot pin 144 (via longitudinal reciprocation of the outer shaft member 160) independent of the inner actuation member 180. Distally of the longitudinal recess 190, the cam pin 192 is mechanically coupled (e.g., via welding, friction-fit, laser welding, etc.) to the distal portion 186 of the inner actuation member 180. A proximal portion 188 of the inner actuation member 180 includes a washer 187 coupled thereto (FIG. 10). The washer 187 is supported within the housing 112 and serves to prohibit longitudinal motion of the inner actuation member 180 parallel to the longitudinal axis A-A.

The jaw members 130, 132 may be pivoted about the pivot pin 144 to move the end effector 114 to the closed configuration of FIG. 2B wherein the sealing plates 148, 150 provide a pressure to tissue grasped therebetween. In some embodiments, to provide an effective seal, a pressure within a range between about 3 kg/cm$^2$ to about 16 kg/cm$^2$ and, desirably, within a working range of 7 kg/cm$^2$ to 13 kg/cm$^2$ is applied to the tissue. Also, in the closed configuration, a separation or gap distance "G" may be maintained between the sealing plates 148, 150 by an array of stop members 154 (FIG. 2A) disposed on or adjacent the sealing plates 148, 150. The stop members 154 contact opposing surfaces on the opposing jaw member 130, 132 and prohibit further approximation of the sealing plates 148, 150. In some embodiments, to provide an effective tissue seal, an appropriate gap distance of about 0.001 inches to about 0.010 inches and, desirably, between about 0.002 and about 0.005 inches may be provided. In some embodiments, the stop members 154 are constructed of an electrically non-conductive plastic or other material molded onto the jaw members 130, 132, e.g., by a process such as overmolding or injection molding. In other embodiments, the stop members 154 are constructed of a heat-resistant ceramic deposited onto the jaw members 130, 132.

Electrosurgical energy may be delivered to the tissue through the electrically conductive seal plates 148, 150 to effect a tissue seal. Once a tissue seal is established, a knife blade 156 having a sharp distal cutting edge 157 may be advanced through a knife channel 158 defined in one or both jaw members 130, 132 to transect the sealed tissue. Knife blade 156 is depicted in FIG. 2A as extending from the elongated shaft 116 when the end effector 114 is in an open configuration. In some embodiments, a knife lockout is provided to prevent extension of the knife blade 156 into the knife channel 158 when the end effector 114 is in the open configuration.

The proximal portion 166 of the outer shaft member 160 includes various features that serve to couple the outer shaft member 160 to various elements of the housing 112. More specifically, the proximal portion 166 of the outer shaft member 160 includes, in order from distal to proximal, a longitudinal slot 169 extending distally from a proximal end thereof to couple the outer shaft member 160 to the rotation knob 128, a longitudinal knife slot 168 defined therethrough, a pair of opposing distal locking slots 161a, 161b, and a pair of opposing proximal locking slots 171a, 171b. The connection established between the outer shaft member 160 and the rotation knob 128 is described below with reference to FIG. 4.

Figure 8:
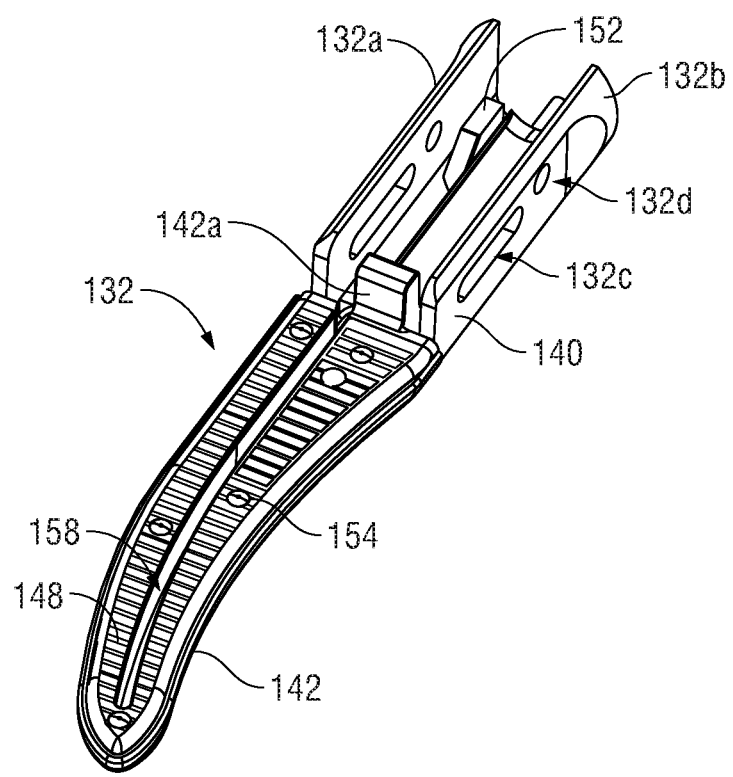
FIG. 8 is a top, perspective view of a lower jaw member of the end effector of FIG. 1.

The pivot pin 144 extends through a proximal portion of each of the jaw members 130, 132 to pivotally support the jaw members 130, 132 at the distal end of the outer shaft member 160. With reference to FIG. 8, a proximal portion of each of the jaw members 130, 132 includes two laterally spaced parallel flanges or "flags" 130a, 130b and 132a, 132b respectively, extending proximally from a distal portion of the jaw members 130 and 132. A lateral cam slot 130c and a lateral pivot bore 130d extend through each of the flags 130a, 130b of the upper jaw member 130. Similarly, a lateral cam slot 132c and a lateral pivot bore 132d extend through each of the flags 132a, 132b of the lower jaw member 132. The pivot bores 130d, 132d receive the pivot pin 144 in a slip-fit relation that permits the jaw members 130, 132 to pivot about the pivot pin 144 to move the end effector 114 between the open and closed configurations (FIGS. 2A and 2B, respectively).

A knife rod 102 is coupled (e.g., via welding) at a distal-most end to the sharpened knife blade 156 and includes an angled proximal end 108 that provides a mechanism for operatively coupling the knife rod 102 to the trigger 126. The connection between the knife rod 102 and the trigger 126 is described in detail below with reference to FIGS. 10, 11, 12A, and 12B. The sharp edge 157 of the knife blade 156 may be applied to the distal end of the knife blade 156 subsequent to the stamping process that forms the profile. For example, various manufacturing techniques may be employed such as grinding, coining, electrochemical etching, electropolishing, or other suitable manufacturing processes, for forming sharpened edges.

Referring to FIGS. 3A and 3B, a tube guide 109 is disposed within the outer shaft member 160 and includes a guide lumen 107 axially disposed therethrough and a longitudinal guide recess 105 formed therein. The inner actuation member 180 is received within the guide lumen 107, which serves to orient and align the inner actuation member 180 within the outer shaft member 160. The knife rod 102 is received within the longitudinal recess 105, which serves to guide longitudinal motion of the knife rod 102 within the outer shaft member 160. In this way, the inner actuation member 180 and the knife rod 102 are aligned within the outer shaft member 160 by the tube guide 109 such that the knife rod 102 is free to move longitudinally relative to the inner actuation member 180.

Figure 4:
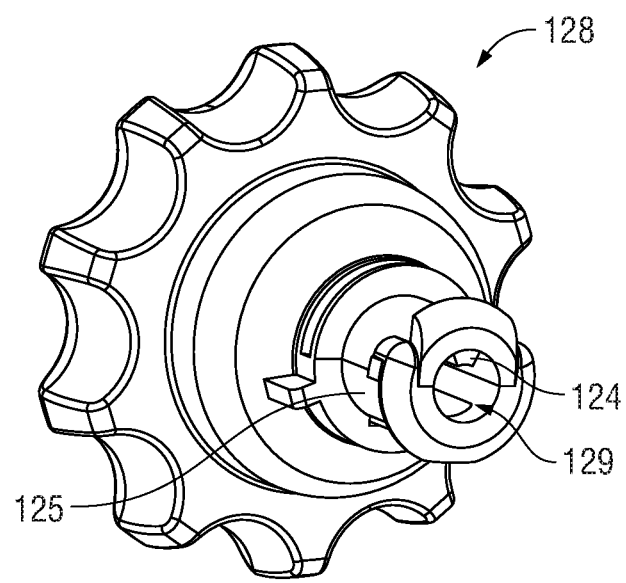
FIG. 4 is a proximally-facing, perspective view of a rotation knob depicting a passageway for receiving the elongated shaft of FIG. 1.

Referring now to FIG. 4, the rotation knob 128 includes a passageway 129 defined therethrough for receiving the outer shaft member 160. The passageway 129 has a generally circular profile corresponding to the circular profile of the outer shaft member 160. The passageway 129 includes a longitudinal keying member 124 that is configured to align with and be seated within longitudinal slot 169 (FIG. 3A) of the outer shaft member 160. The keying member 124 projects laterally inward along the length of passageway 129 such that the insertion of the proximal end of the outer shaft member 160 into the passageway 129 of the rotation knob 128 operatively couples the outer shaft member 160 to the rotation knob 128. Rotational motion imparted to the rotation knob 128 may thus impart rotational motion to each of the components of the elongated shaft 116, and to the end effector 114, which is coupled thereto. As shown in FIG. 12, the rotation knob 128 is seated within an interior compartment 134 of the housing 112 and, as shown in FIG. 1, extends laterally outward from opposing sides of the housing 112 (only shown extending laterally outward from housing half 112b).

Figure 5:
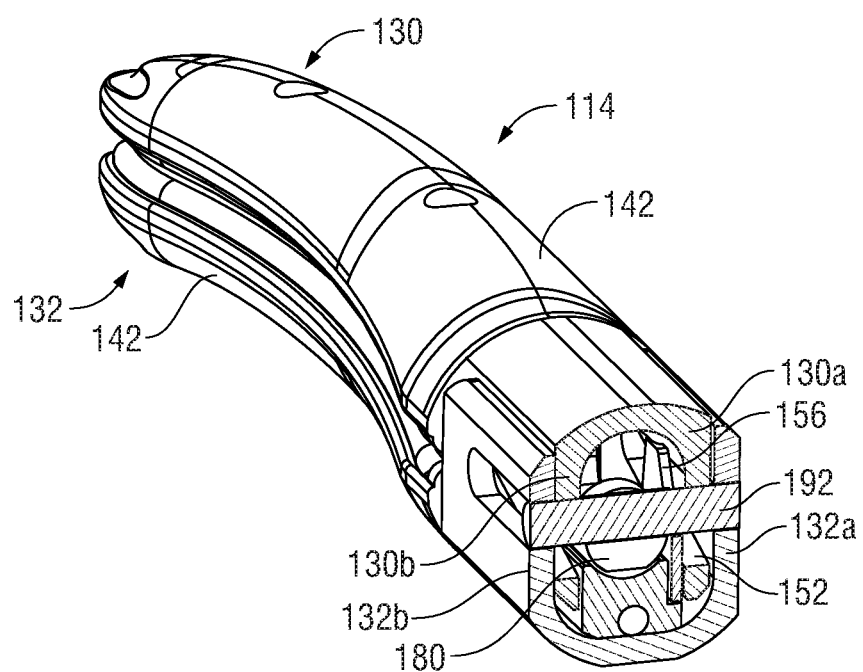
FIG. 5 is a cross-sectional, perspective view of the end effector of FIG. 1.

Referring now to FIG. 5, the end effector 114 is coupled to the distal end of the inner actuation member 180 by the cam pin 192. The cam pin 192 represents a longitudinally stationary reference for the longitudinal movements of the outer shaft member 160, the pivot pin 144, and the knife rod 102. The cam pin 192 extends through the flags 132a, 132b of the lower jaw member 132 and the flags 130a and 130b of the upper jaw member 130.

Figure 6:
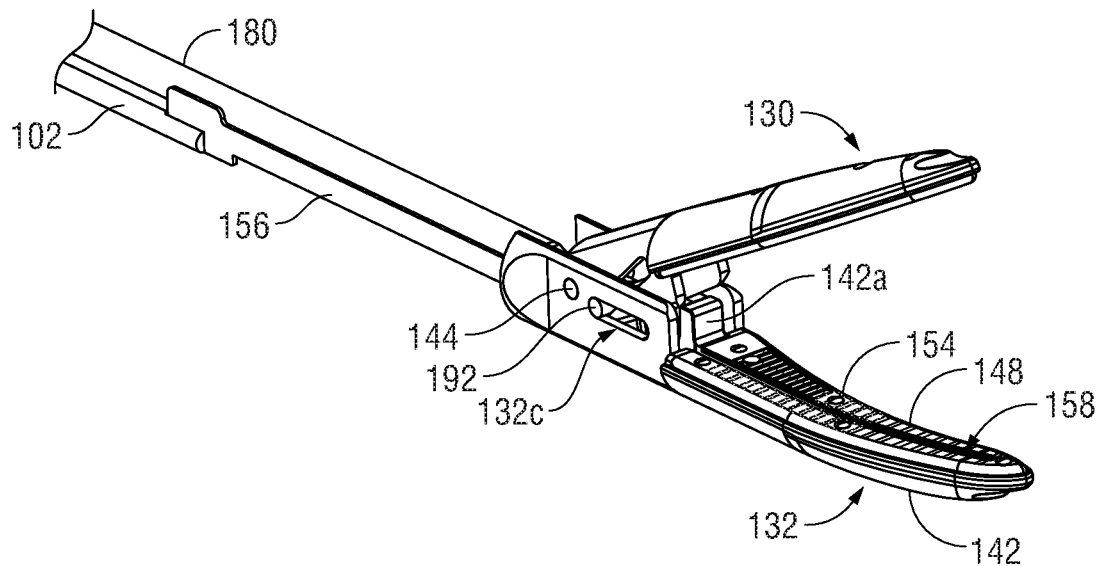
FIG. 6 is a partial, proximal-facing perspective view of a distal portion of a jaw actuation mechanism of the end effector of FIG. 1.

Referring now to FIG. 6, the end effector 114 is shown in the open configuration. Since the inner actuation member 180 is coupled to the cam pin 192, when the outer shaft member 160 is in the distal position (unactuated) and the inner actuation member 180 is in the proximal position relative to the outer shaft member 160, the cam pin 192 is located in a proximal position in cam slots 130c and 132c defined through the flags 130a, 130b, 132a, 132b of the jaw members 130, 132, respectively.

The outer shaft member 160 may be drawn proximally relative to the inner actuation member 180 and the cam pin 192 to move the end effector 114 to the closed configuration (see FIG. 2B). Since the longitudinal position of the cam pin 192 is fixed, and since the cam slots 130c, 132c are obliquely arranged with respect to the longitudinal axis A-A, proximal retraction of the outer shaft member 160 induces distal translation of the cam pin 192 through the cam slots 130c, 132c and jaw member 130 to pivot toward jaw member 132 about the pivot pin 144. Conversely, when the end effector 114 is in the closed configuration, longitudinal translation of the outer shaft member 160 in a distal direction induces proximal translation of the cam pin 192 through the cam slots 130c, 132c and jaw member 130 to pivot away from jaw member 132 toward the open configuration.

Figure 7:
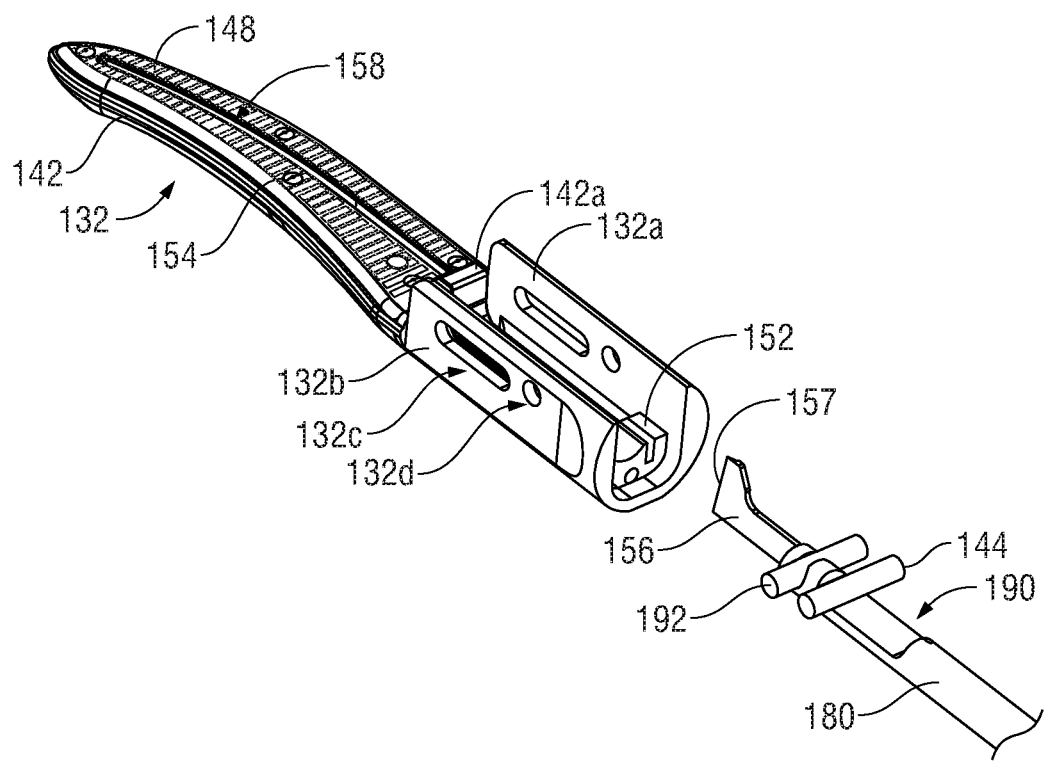
FIG. 7 is a partial, distal-facing perspective view of distal portion of a knife actuation mechanism of the end effector of FIG. 1.

Referring now to FIG. 7, the pins 144, 192 do not interfere with the reciprocal motion of the knife blade 156. A proximal portion of the insulator 142 forms a blade guide 142a (also see FIGS. 8 and 9) that serves to align the knife blade 156 such that the knife blade 156 readily enters the knife channel 158 defined in the jaw members 130, 132 (jaw member 130 removed from view in FIG. 7 for clarity).

Figure 9:
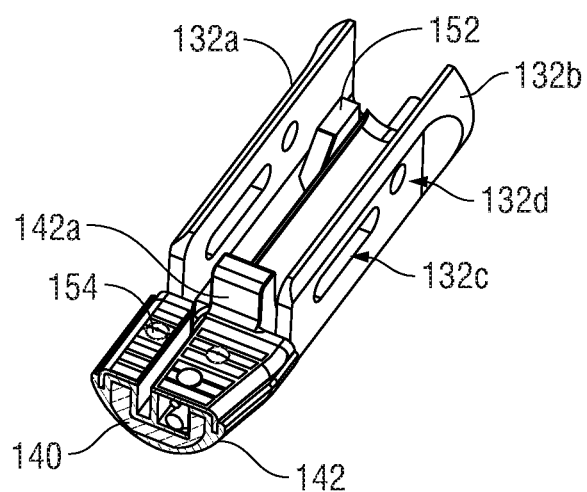
FIG. 9 is a top, cross-sectional, perspective view of the lower jaw member of FIG. 8.

Referring now to FIGS. 8 and 9, the lower jaw member 132 is constructed of three major components. These components include the jaw insert 140, the insulator 142, and the sealing plate 148. The flags 132a, 132b of the jaw member 132 define a proximal portion of the jaw insert 140 and a generally u-shaped profile of the jaw insert 140 extends distally to support the tissue engaging portion of the jaw member 132. Upper jaw member 130 includes the same three major components as lower jaw member 132, including sealing plate 150, and is constructed in the same manner as lower jaw member 132.

The insulator 142 may be constructed of an electrically insulative plastic such as a polyphthalamide (PPA) (e.g., Amodel®), polycarbonate (PC), acrylonitrile butadiene styrene (ABS), a blend of PC and ABS, nylon, ceramic, etc. The electrically insulative plastic may be overmolded onto the jaw insert 140 in a single-shot injection molding process such that sealing plate 148 is overmolded to the jaw insert 140. Additionally or alternatively, the electrically insulative plastic may be mechanically coupled to the jaw insert 140, e.g., pressed, snapped, glued, etc. Various features may be molded into the insulator 142 that facilitate the attachment of the sealing plate 148 to the insert 140. For example, tabs may be provided that permit a snap-fit attachment of the sealing plate 148, or ridges may formed that permit ultrasonic welding of the sealing plate 148 onto the insulator 142. The sealing plate 148 may be constructed of an electrically conductive metal, and may be stamped from a flat sheet stock.

Referring now to FIG. 10, the connection of the movable handle 122 and the knife trigger 126 to the longitudinally movable components of the elongated shaft 116 is described. The movable handle 122 may be manipulated to impart longitudinal motion to the outer shaft member 160, and the knife trigger 126 may be manipulated to impart longitudinal motion to the knife rod 102. As discussed above, longitudinal motion of the outer shaft member 160 serves to move the end effector 114 between the open configuration of FIG. 2A and the closed configuration of FIG. 2B, and longitudinal motion of the knife rod 102 serves to move knife blade 156 through knife channel 158 (FIG. 2A).

Figure 11:
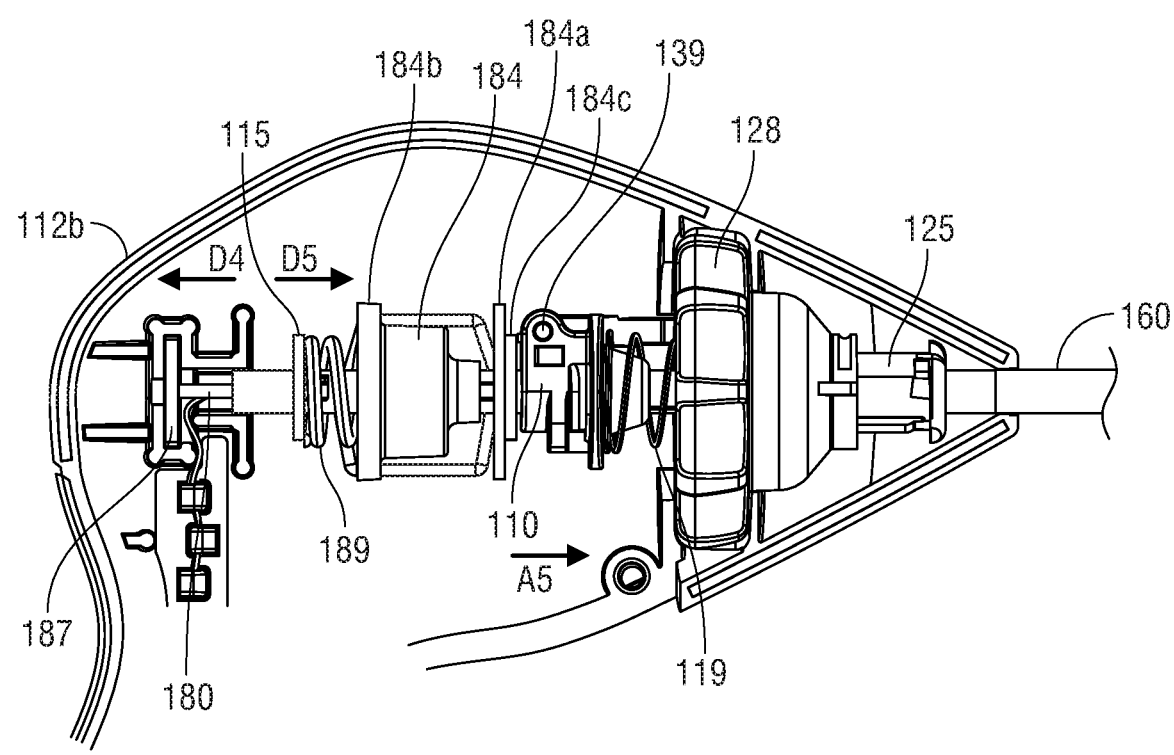
FIG. 11 is a partial, side view of a proximal portion of the instrument of FIG. 1.

The movable handle 122 is operatively coupled to the outer shaft member 160 by clevis 178 defined at an upper end of the movable handle 122. The clevis 178 is pivotally supported on the left housing half 112b by a pivot boss 179. A second complementary pivot boss (not shown) is provided on the right housing half 112a to support the clevis 178. The clevis 178 extends upwardly about opposing sides of a drive collar 184 (FIG. 11) supported on the outer shaft member 160 and includes rounded drive surfaces 197a and 197b thereon. Drive surface 197a engages a proximal-facing surface of a distal spring washer 184a and drive surface 197b engages a distal facing surface of a proximal rim 184b of the drive collar 184 (FIG. 11). The distal spring washer 184a engages a proximal facing surface of a distal spring stop 184c that, in turn, engages the opposing distal locking slots 161a, 161b (FIG. 3A) extending through the proximal portion 166 (FIG. 3A) of the outer shaft member 160 to couple the distal spring stop 184c to the outer shaft member 160. The drive surfaces 197a, 197b are arranged along the longitudinal axis A-A such that pivotal motion of the movable handle 122 induces corresponding longitudinal motion of the drive collar 184 (FIG. 11) along the longitudinal axis A-A.

Referring now to FIG. 11, proximal longitudinal motion may be imparted to the outer shaft member 160 by pushing the proximal rim 184b of the drive collar 184 proximally with the movable handle 122 (FIG. 10) as indicated by arrow D4 (FIG. 11). A spring 189 is constrained between a proximal facing surface of the drive collar 184 and a proximal spring stop 115. The proximal spring stop 115 engages the opposing proximal locking slots 171a, 171b (FIG. 3A) extending through the proximal portion 166 (FIG. 3A) of the outer shaft member 160 to couple the proximal spring stop 115 to the outer shaft member 160. Thus, the proximal spring stop 115 serves as a proximal stop against which spring 189 compresses.

Distal longitudinal motion is imparted to the outer shaft member 160 by driving the drive collar 184 distally with the movable handle 122 as indicated by arrow D3 (FIG. 10). Distal longitudinal motion of the drive collar 184 induces a corresponding distal motion of the outer shaft member 160 by virtue of the coupling of the drive collar 184 to opposing distal locking slots 181a, 181b extending through the proximal portion 166 of the outer shaft member 160 (FIG. 3A).

Proximal longitudinal motion of the outer shaft member 160 draws jaw member 132 proximally such that the cam pin 192 advances distally to pivot jaw member 130 toward jaw member 132 to move the end effector 114 to the closed configuration as described above with reference to FIG. 6. Once the jaw members 130 and 132 are closed, the outer shaft member 160 essentially bottoms out (i.e., further proximal movement of the outer shaft member 160 is prohibited since the jaw members 130, 132 contact one another). Further proximal movement of the movable handle 122 (FIG. 10), however, will continue to move the drive collar 184 proximally. This continued proximal movement of the drive collar 184 further compresses the spring 189 to impart additional force to the outer shaft member 160, which results in additional closure force applied to tissue grasped between the jaw members 130, 132 (see FIG. 2B).

Referring again to FIG. 10, the trigger 126 is pivotally supported in the housing 112 about a pivot boss 103 protruding from the trigger 126. The trigger 126 is operatively coupled to the knife rod 102 by a knife connection mechanism 104 such that pivotal motion of the trigger 126 induces longitudinal motion of the knife rod 102. The knife connection mechanism 104 includes upper flanges 126a, 126b of the trigger 126 and a knife collar 110.

Figure 12A:
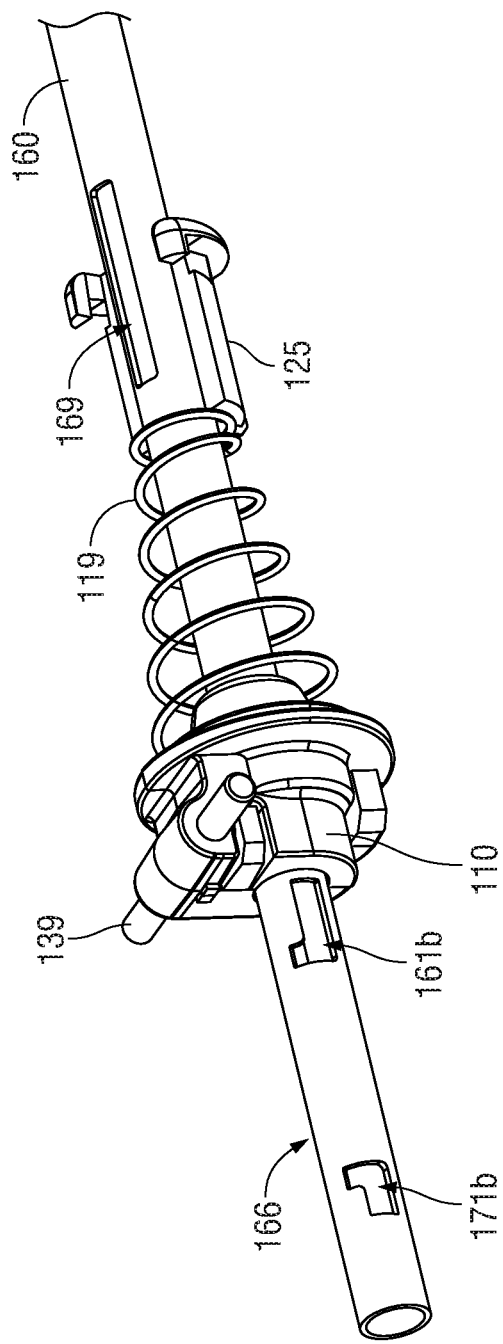
FIG. 12A is an enlarged, perspective view of a proximal portion of the knife actuation mechanism of the end effector of FIG. 1.
Figure 12B:
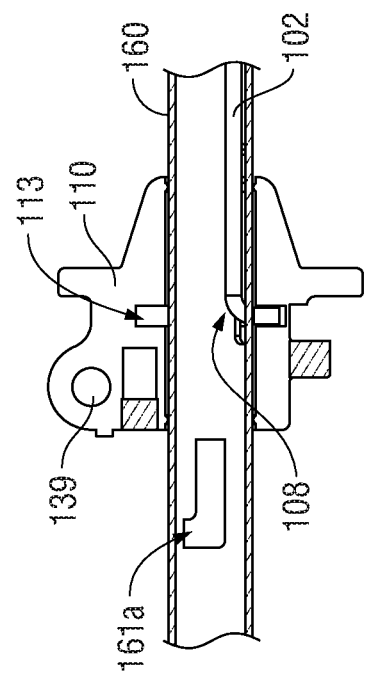
FIG. 12B is an enlarged, cross-sectional, side view of a knife collar of the knife actuation mechanism of the end effector of FIG. 1.

Referring now to FIGS. 11, 12A, and 12B, the knife collar 110 includes a pair of integrally formed pin bosses 139a, 139b extending from opposing sides thereof. As shown by FIG. 12B, the knife collar 110 includes an interior circular channel 113 that captures the angled proximal end 108 of the knife rod 102 to couple the knife rod 102 to the knife collar 110. Upon longitudinal motion of the outer shaft member 160, the angled proximal end 108 of the knife rod 102 translates longitudinally within the knife slot 168 (FIG. 3A) of the outer shaft member 160 such that the longitudinal motion of outer shaft member 160 is unimpeded by the angled proximal end 108 of the knife rod 102. Upon rotation of the elongated shaft 116 and end effector 114 about the longitudinal axis A-A via the rotation knob 128 (FIG. 1), the angled proximal end 108 of the knife rod 102 freely rotates within the interior circular channel 113 of the knife collar 110 such that the outer and inner actuation members 160 and 180 (removed from view in FIG. 12B for clarity), and the knife rod 102 rotate within the knife collar 110 about the longitudinal axis A-A. In this way, the knife collar 110 serves as a stationary reference for the rotational movement of the outer shaft member 160, the inner actuation member 180, and the knife rod 102.

Referring again to FIG. 10, the upper flanges 126a, 126b of the trigger 126 include respective slots 127a, 127b defined therethrough that are configured to receive the pin bosses 139a, 139b, respectively, of the knife collar 110 such that pivotal motion of the trigger 126 induces longitudinal motion of the knife collar 110 and, thus, the knife rod 102 by virtue of the coupling of knife rod 102 to the knife collar 110.

Referring now to FIGS. 11 and 12A, when the trigger 126 is moved to induce motion of the knife collar 110 in order to translate the blade 156 through the knife channel 158, the knife collar 110 translates along the outer shaft member 160 in the direction of arrow A5 to abut a spring 119 such that spring 119 compresses against an interior portion of the rotation knob 128 (FIG. 10). The spring 119 biases the knife collar 110 proximally along the outer shaft member 160.

Figure 13A:
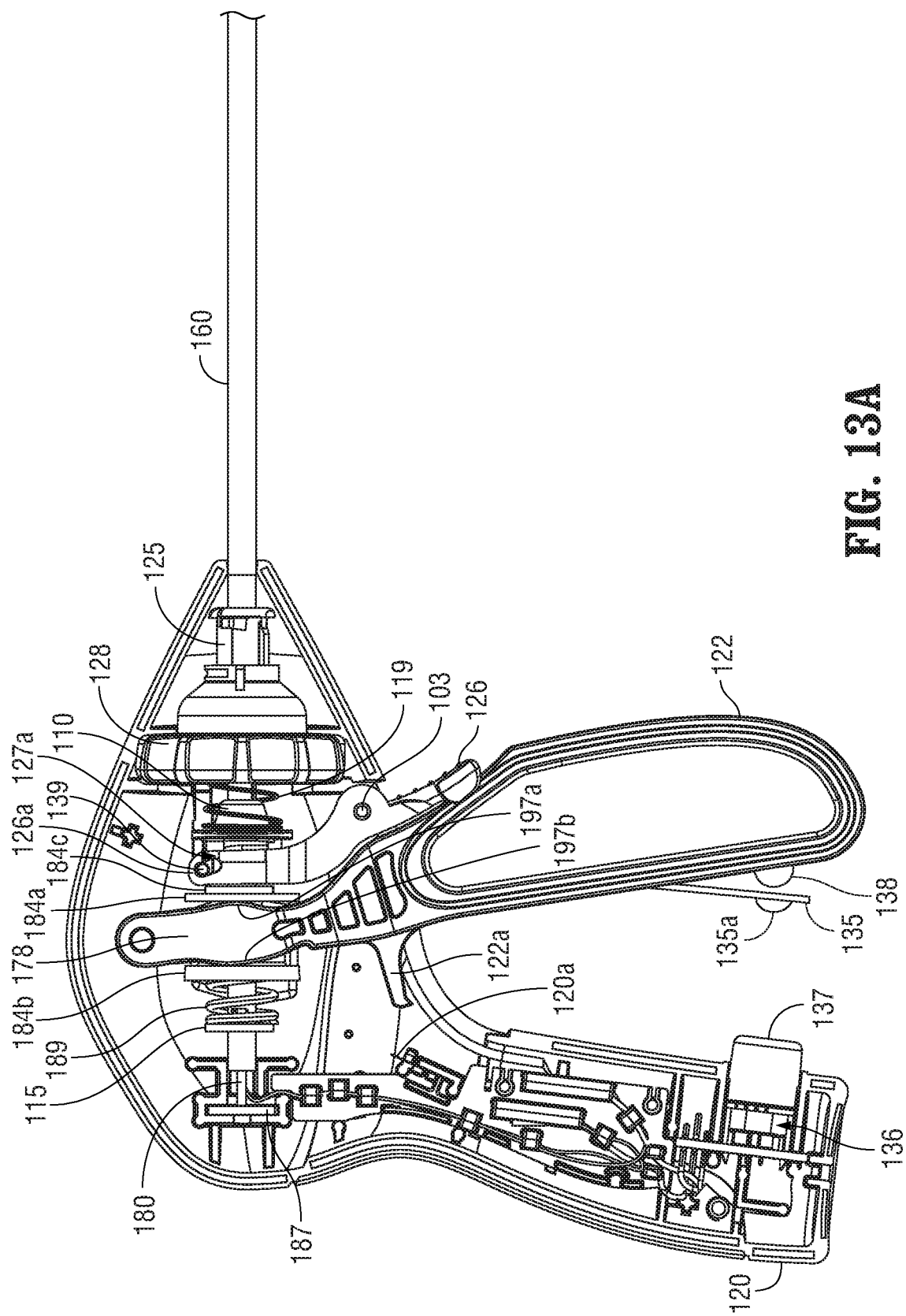
FIG. 13A is an internal, side view of the proximal portion of the instrument of FIG. 10 depicting a movable handle in a separated position with respect to a stationary handle, which corresponds to the open configuration of the end effector depicted in FIG. 2A, and a knife trigger in a separated configuration with respect to the stationary handle, which corresponds to an un-actuated or proximal configuration of a knife with respect to the jaw members.

As indicated above with respect to the embodiment depicted in FIG. 10, the forceps 100 may include an enhanced switch control feature configured to prevent the deactivation and reactivation of the switch 136 to terminate and reinitiate, respectively, the delivery of electrosurgical energy to the end effector 114 during operation of the trigger 126. With reference to FIGS. 13A, 13B, 13C, and 13D, another such embodiment is depicted, wherein a spring lever 135 (e.g., leaf spring) extends from a proximal side of the moveable handle 122 and includes an activation post 135a configured to engage and depress the button 137 upon approximation of the moveable handle 122 with the stationary handle 120 (FIG. 13C). The spring lever 135 is biased away from the surface of the moveable handle 122 from which it extends such that upon approximation of the moveable handle 122 with the stationary handle 120, the button activation post 135a engages and depresses the button 137 and a spring force is applied on the button 137 by the spring lever 135. Upon further approximation of the moveable handle 122 with the stationary handle 120, the button activation post 138 engages the spring lever 135 to cause the activation post 135a to apply additional force on the button 137. If the moveable handle 122 inadvertently moves distally away from the stationary handle 120 (e.g., during operation of the trigger 126), as depicted by arrow M7 in FIG. 13D, the spring lever 135 serves to mitigate the effects of this distal movement of the moveable handle 122 by maintaining a spring force on the button 137. This spring force maintained on the button 137 is sufficient to keep the switch 136 activated during at least a portion of travel of the moveable handle 122 in the distal direction (arrow M7), such that the switch 136 is not deactivated and reactivated during operation of the trigger 126. As the moveable handle 122 moves farther away from the stationary handle 120 to move the end effector 114 to the open configuration (FIG. 13A), the spring force maintained on the button 137 by the spring lever 135 relents and, as a result, the switch 136 is deactivated.

Referring again to FIGS. 13A, 13B, 13C and 13D, a sequence of motions may be initiated by moving the movable handle 122 to induce motion of the outer shaft member 160 in order to close the jaws 130, 132, and by moving the trigger 126 to induce motion of the knife collar 110 in order to translate the blade 156 through the knife channel 158. Initially, both the moveable handle 122 and the knife trigger 126 are in a distal or un-actuated position as depicted in FIG. 13A. This arrangement of the moveable handle 122 and trigger 126 sustains the end effector 114 in the open configuration (FIG. 2A) wherein the jaw members 130, 132 are substantially spaced from one another, and the knife blade 156 is in a retracted or proximal position with respect to the jaw members 130, 132. When both the moveable handle 122 and the knife trigger 126 are in the distal, un-actuated position, pivotal motion of the knife trigger 126 in a proximal direction, i.e., toward the stationary handle 120, is prohibited by interference between the trigger 126 and moveable handle 122. This interference prohibits advancement of the knife blade 156 through the knife channel 158 when the end effector 114 is in the open configuration.

Figure 13B:
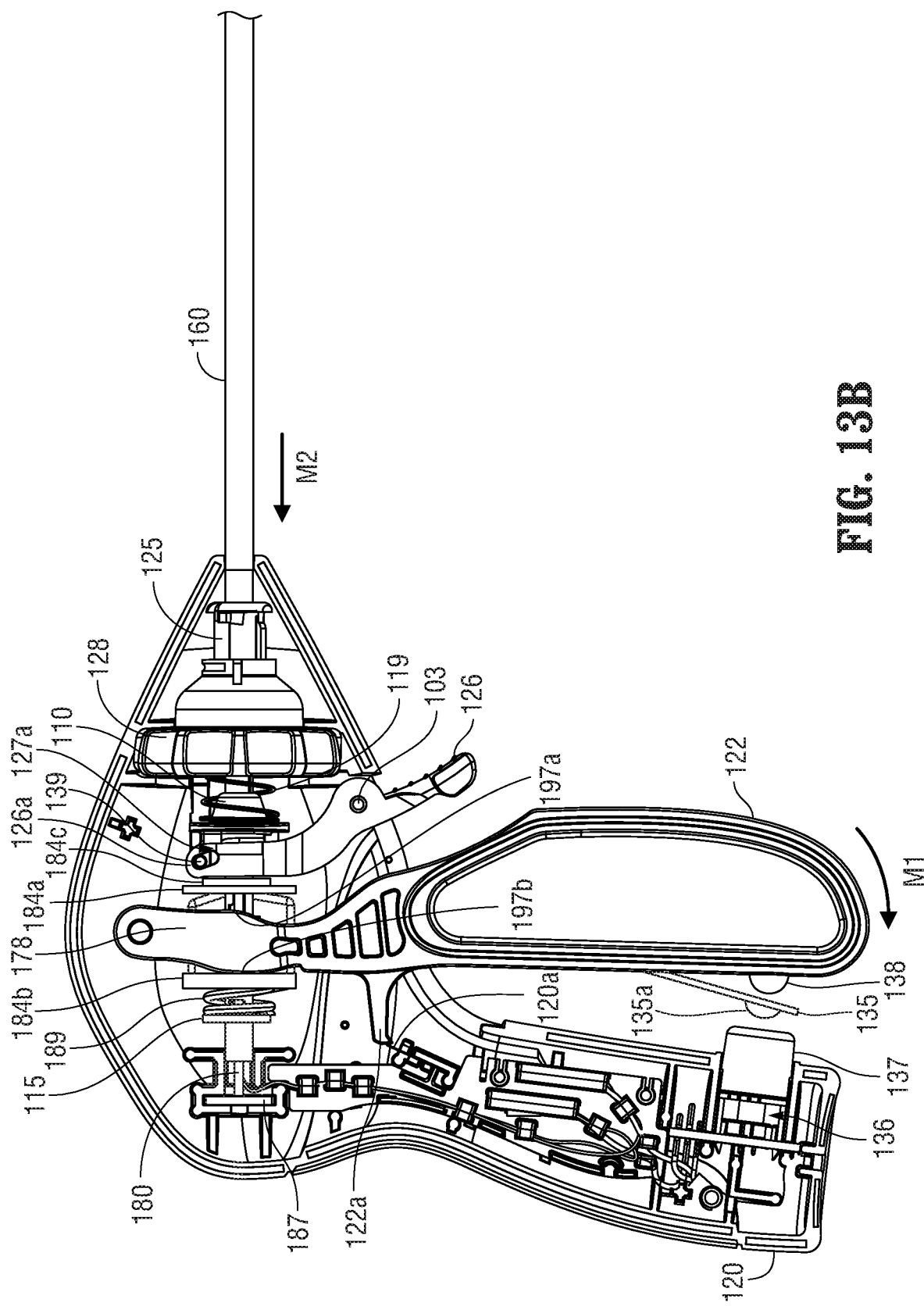
FIG. 13B is an internal, side view of the proximal portion of the instrument of FIG. 10 depicting the movable handle in an intermediate position with respect to the stationary handle, which corresponds to a first closed configuration of the end effector wherein the jaw members encounter one another.
Figure 13C:
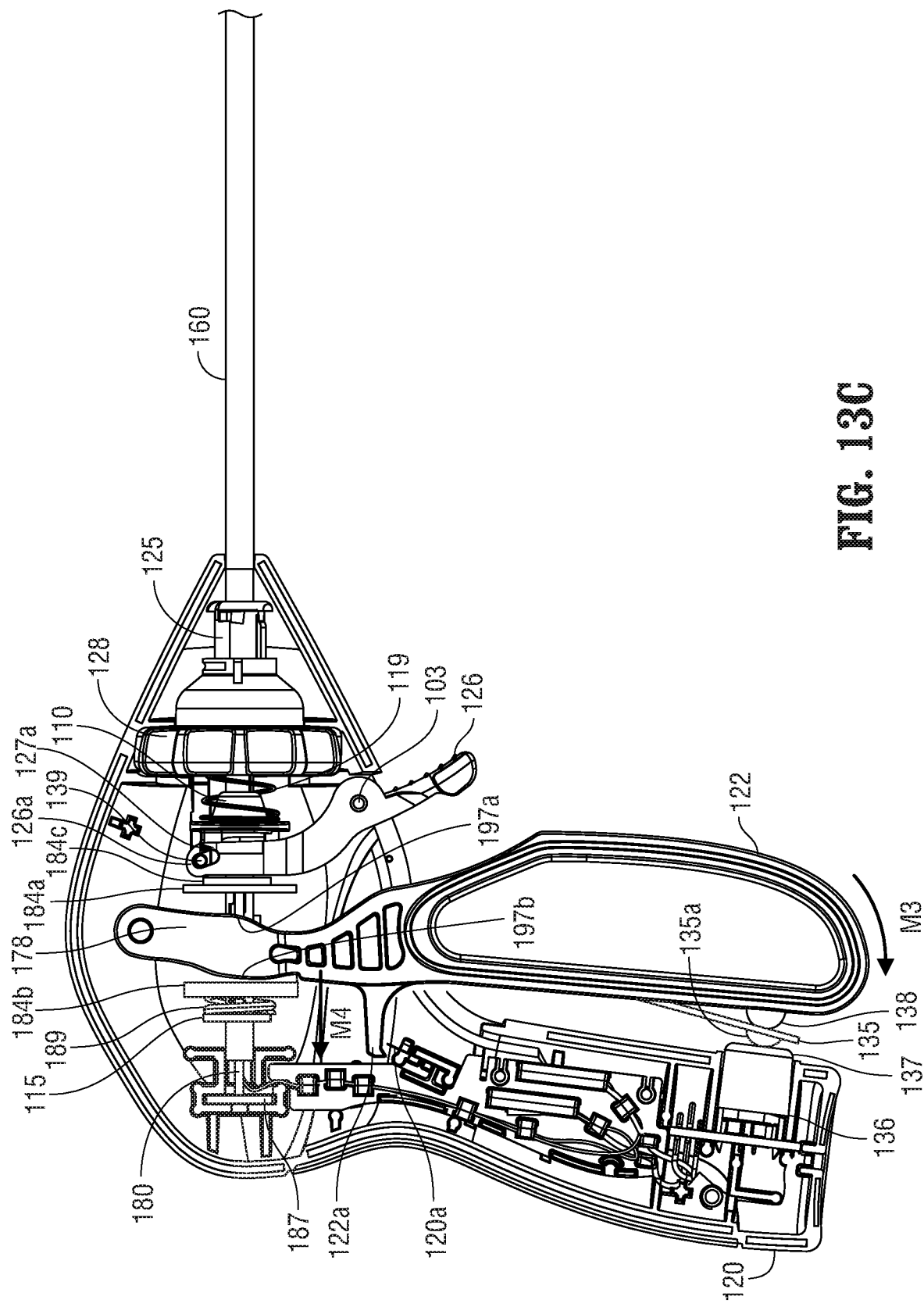
FIG. 13C is an internal, side view of the proximal portion of the instrument of FIG. 10 depicting the movable handle in an approximated configuration with respect to the stationary handle, which corresponds to a second closed configuration of the end effector wherein the jaw members apply an appropriate pressure to generate a tissue seal.

The movable handle 122 may be moved from the distal position of FIG. 13A to an intermediate position depicted in FIG. 13B to move the jaw members 130, 132 to the closed configuration (FIG. 2B). As the movable handle 122 pivots in the direction of arrow M1 (FIG. 13B), the drive surface 197b of the movable handle 122 engages the proximal rim 184b of the drive collar 184. The drive collar 184 is driven proximally such that the spring 189 proximally biases the proximal spring stop 115 and, thus, the outer shaft member 160 is driven proximally in the direction of arrow M2 (FIG. 13B). As discussed above with reference to FIG. 6, proximal movement of the outer shaft member 160 serves to advance the cam pin 192 distally though the cam slots 130c, 132c (FIG. 3A) of the jaw members 130, 132, respectively, and thus pivot jaw member 130 toward jaw member 132 (FIG. 2B). As the jaw members 130, 132 engage one another and no further pivotal movement of the jaw members 130, 132 may be achieved, further distal movement of the cam pin 192 and further proximal movement of the outer shaft member 160 are prevented.

As the movable handle 122 is moved from the distal position of FIG. 13A to the intermediate position depicted in FIG. 13B, a tooth 122a extending proximally from an upper portion of the moveable handle 122 engages a clicker tab 120a supported within the stationary handle 120 to generate a tactile and/or audible response. This response generated by the clicker tab 120a corresponds to a complete grasping of tissue between the jaw members 130, 132 and serves to indicate to the surgeon that further proximal actuation of the moveable handle 122 will cause the button activation post 135a to engage the depressible button 137. As the moveable handle 122 is moved from the intermediate position of FIG. 13B to the actuated or proximal position of FIG. 13C, the tooth 122a is positioned proximally of the clicker tab 120a and the button activation post 135a depresses the depressible button 137, thereby activating the switch 136 disposed within the stationary handle 120 to initiate the delivery of electrosurgical energy to the end effector 114 to generate a tissue seal or otherwise treat tissue.

As the movable handle 122 is moved from the intermediate position of FIG. 13B to the actuated or proximal position of FIG. 13C, the pressure applied by the jaw members 130, 132 is increased. As the movable handle 122 pivots further in the direction of arrow M3 (FIG. 13C), the drive surface 197b presses the proximal rim 184b of the drive collar 184 further proximally against the spring 189 in the direction of arrow M4 (FIG. 13C). The spring 189 is compressed against the proximal spring stop 115, and a tensile force is transmitted through the outer shaft member 160 to the jaw members 130, 132. The tensile force supplied by the spring 189 ensures that the jaw members 130, 132 apply an appropriate pressure to effect a tissue seal.

When the movable handle 122 is in the actuated or proximal position, the knife trigger 126 may be selectively moved from the distal position of FIG. 13C to the proximal position of FIG. 13D to advance the knife blade 156 distally through knife channel 158. The knife trigger 126 may be pivoted in the direction of arrow M5 (FIG. 13D), about pivot boss 103 to advance the flanges 126a, 126b of the knife trigger 126 distally in the direction of arrow M6 such that the pin boss 139b translates within slot 127b from the position shown in FIGS. 13A-13C to the position shown in FIG. 13D. Although not explicitly shown in FIGS. 13A-13D, pin boss 139a translates within slot 127a in the same manner as described above with respect to pin boss 139b and slot 127b. Movement of flanges 126a, 126b draws the knife collar 110 distally, which induces distal longitudinal motion of the knife rod 102 by virtue of the coupling of the knife rod 102 to the knife collar 110, as described above with reference to FIG. 12B.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
a housing;
a switch coupled to the housing;
a handle coupled to the housing and movable between an actuated position and an unactuated position; and
a switch controller disposed on the handle, the switch controller biased into engagement with the switch by the handle upon movement of the handle to the actuated position to move the switch from an unactivated configuration to an activated configuration, the switch controller maintaining the switch in the activated configuration during movement of the handle from the actuated position toward the unactuated position.

2. The surgical instrument according to claim 1, further comprising an elongated shaft extending from the housing, the handle configured to move the elongated shaft longitudinally upon movement of the handle between the actuated and unactuated positions.

3. The surgical instrument according to claim 2, further comprising first and second jaw members disposed at a distal end portion of the elongated shaft, at least one of the first or second jaw members configured to move relative to the other upon longitudinal movement of the elongated shaft.

4. The surgical instrument according to claim 3, wherein movement of the handle moves the elongated shaft longitudinally relative to a stationary actuation shaft axially disposed within the elongated shaft to move at least one of the first or second jaw members relative to the other.

5. The surgical instrument according to claim 1, wherein the handle includes an upper portion disposed within the housing and a lower portion disposed exterior to the housing, the lower portion of the handle configured to bias the switch controller into engagement with the switch upon movement of the handle to the actuated position to move the switch from the unactivated configuration to the activated configuration.

6. The surgical instrument according to claim 1, wherein the handle is configured to move in a distal direction toward the unactuated position.

7. The surgical instrument according to claim 1, wherein the handle is configured to move in a proximal direction toward the actuated position.

8. The surgical instrument according to claim 1, further comprising a switch activation post extending from the handle and configured to bias the switch controller into engagement with the switch upon movement of the handle to the actuated position.

9. The surgical instrument according to claim 8, wherein the switch activation post is configured to disengage the switch controller during movement of the handle toward the unactuated position such that the switch controller moves out of biased engagement with the switch and the switch moves from the activated configuration to the unactivated configuration.

10. The surgical instrument according to claim 1, further comprising a knife blade configured to move along a longitudinal axis defined by the surgical instrument to cut tissue.

11. A surgical instrument, comprising:
a housing;
a button extending from the housing and coupled to a switch;
a handle coupled to the housing and movable between an actuated position and an unactuated position, the handle including an upper portion disposed within the housing and a lower portion disposed exterior to the housing; and
a switch controller disposed on the lower portion of the handle, the switch controller biased into engagement with the button by the lower portion of the handle upon movement of the handle to the actuated position such that the button moves relative to the housing to activate the switch, the switch controller causing the switch to remain activated during movement of the handle from the actuated position toward the unactuated position.

12. The surgical instrument according to claim 11, further comprising a switch activation post extending from the lower portion of the handle and configured to bias the switch controller into engagement with the button upon movement of the handle to the actuated position.

13. The surgical instrument according to claim 12, wherein the switch activation post is configured to disengage the switch controller during movement of the handle toward the unactuated position such that the switch controller moves out of biased engagement with the button and the button moves relative to the housing to deactivate the switch.

14. The surgical instrument according to claim 11, further comprising a knife blade configured to move along a longitudinal axis defined by the surgical instrument to cut tissue.

15. The surgical instrument according to claim 11, further comprising an elongated shaft extending from the housing, the handle configured to move the elongated shaft longitudinally upon movement of the handle between the actuated and unactuated positions.

16. The surgical instrument according to claim 15, further comprising first and second jaw members disposed at a distal end portion of the elongated shaft, at least one of the first or second jaw members configured to move relative to the other upon longitudinal movement of the elongated shaft.

17. The surgical instrument according to claim 16, wherein movement of the handle moves the elongated shaft longitudinally relative to a stationary actuation shaft axially disposed within the elongated shaft to move at least one of the first or second jaw members relative to the other.

18. A surgical instrument, comprising:
a housing including a stationary handle;
a switch coupled to the stationary handle;
a movable handle coupled to the housing and movable relative to the stationary handle; and
a switch controller disposed on the movable handle, the switch controller biased into engagement with the switch by the movable handle upon approximation of the movable handle with the stationary handle to activate the switch, the switch controller causing the switch to remain activated during movement of the movable handle away from the stationary handle.

19. The surgical instrument according to claim 18, wherein the switch controller is configured to disengage the switch during movement of the moveable handle away from the stationary handle such that the switch is deactivated.

20. The surgical instrument according to claim 18, wherein the switch controller is configured to be:
maintained in biased engagement with the switch by the movable handle during a first portion of movement of the movable handle away from the stationary handle thereby causing the switch to remain activated; and disengaged from the switch during a second portion of movement of the movable handle away from the stationary handle thereby causing the switch to deactivate.

\* \* \* \* \*